United States Patent [19]
Nisbet et al.

[11] Patent Number: 5,951,977
[45] Date of Patent: Sep. 14, 1999

[54] COMPETITIVE EXCLUSION CULTURE FOR SWINE

[75] Inventors: David J. Nisbet, Bryan; Donald E. Corrier; Larry H. Stanker, both of College Station, all of Tex.

[73] Assignee: The United States of America, as represented by the Secretary of Agriculture, Washington, D.C.

[21] Appl. No.: 08/949,348

[22] Filed: Oct. 14, 1997

[51] Int. Cl.$^6$ .................................................... C12N 1/20
[52] U.S. Cl. .................. 424/93.3; 424/93.48; 424/93.1; 435/252.4
[58] Field of Search ................................ 424/93.3, 93.48, 424/93.1; 435/252.4

[56] References Cited

U.S. PATENT DOCUMENTS

| | | | |
|---|---|---|---|
| 5,340,577 | 8/1994 | Nisbet et al. | 424/93.21 |
| 5,478,557 | 12/1995 | Nisbet et al. | 424/93.21 |
| 5,604,127 | 2/1997 | Nisbet et al. | 435/252.4 |
| 5,807,546 | 9/1998 | Stern et al. | 424/93.3 |

*Primary Examiner*—Jean C. Witz
*Attorney, Agent, or Firm*—M. Howard Silverstein; Randall E Deck; John D Fado

[57] ABSTRACT

A defined probiotic or composition of anaerobic bacteria effective for controlling or inhibiting Salmonella colonization of swine is disclosed. The probiotic includes populations or cultures of substantially biologically pure bacteria which include:

*Enterococcus faecalis*,
*Streptococcus bovis*,
*Clostridium clostridiforme*,
*Clostridium symbiosum*,
*Clostridium ramosum*,
*Bacteroides fragilis*,
*Bacteroides distasonis*,
*Bacteroides vulgatus*,
*Bacteroides thetaiotamicron*, and
*Bacteroides caccae*.

In use, the probiotic is administered to the subject swine in an amount effective for increasing resistance to Salmonella colonization thereof.

18 Claims, No Drawings

COMPETITIVE EXCLUSION CULTURE FOR SWINE

BACKGROUND OF THE INVENTION

1. Field of Invention

This invention relates to defined competitive exclusion cultures or probiotics for the control of Salmonella colonization in swine.

Despite the efforts of researchers and public health agencies, the incidence of human salmonellosis has increased over the past 20 years. The number of actual reported cases of human Salmonella infection exceeds 40,000 per year. However, the Communicable Disease Center estimates that the true incidence of human Salmonella infections in the U.S. each year may be as high as 2 to 4 million. Animal food products, including swine, remain a significant source of human infection.

In addition to the impact of Salmonella on human health, Salmonella infections in swine cost the United States swine industry more than 100 million dollars annually (Schwartz, 1990, "Salmonellosis in Midwestern Swine", In: Proceedings of the United States Animal Health Assoc., pp. 443–449). In the U.S., salmonellosis caused by *S. cholerasuis*, the etiologic agent of swine parathyphoid, occurs most frequently. While pigs can be exposed to a broad host range of salmonellae, such as *S. typhimurium*, from a variety of sources, *S. cholerasuis* is a host adapted pathogen rarely isolated from non-swine sources (Schwartz, ibid). Thus, natural infection of new animals by *S. cholerasuis* occurs primarily via horizontal transmission from infected animals which shed the pathogens from their gastrointestinal tract.

2. Description of the Prior Art

Considering the widespread presence of Salmonella in the environment, it is unlikely that animals can be completely protected from Salmonella exposure. Therefore, researchers have continued to investigate means of increasing resistance to colonization in animals exposed to Salmonella. Studies have focused on the evaluation of vaccines, establishment of protective normal intestinal flora, and the identification of feed additives that will inhibit Salmonella growth and colonization. The role of host immunity against Salmonella colonization is unclear, and it also remains uncertain if stimulation of immune responses will effectively enhance colonization resistance. Experimental vaccines have not proven to be consistently effective.

It is well documented that the development of a normal intestinal microflora can increase resistance against Salmonella colonization of the gastrointestinal tract. In the poultry industry, oral inoculation of young chicks with anaerobic bacterial cultures of microflora, also known as probiotics (defined as bacterial cultures which have a beneficial effect on the animal to which they are administered), prepared from the cecal contents or fecal droppings of mature chickens has proven to effectively reduce Salmonella colonization [Snoeyenbos et al., Avian Dis., 23:904–913, (1979), Schneitz et al., Acta Pathol. Microbiol. Scand. Sect. B., 89:109–116, (1981), and Stavric et al., J. Food Prot., 48:778–782, (1985)]. Conversely, poultry rearing practices that prevent chicks from becoming colonized by these cecal anaerobes make the chicks more susceptible to Salmonella colonization [Pivnick et al., J. Food Prot., 44:909–916, (1981)]. These probiotics may decrease Salmonella colonization by rapidly colonizing the intestinal tract of the young chicks (Pivnick et al., ibid), by competing for attachment sites on the intestinal wall (Snoeyenbos et al., ibid), or by producing bacteriostatic or bactericidal short-chained volatile fatty acids [Barnes et al., J. Hyg. Camb., 82:263–283, (1979) and Am. J. Clin. Nutr., 33:2426–2433, (1980), Corrier et al., Avian Dis., 34:668–676, (1990) and Avian Dis., 34:617–625, (1990), and Hinton et al., Avian Dis., 34:626–633, (1990)] that inhibit the growth of enteropathogens.

Establishment of normal intestinal flora in day-old chicks using mixed cultures of micro-organisms has been widely used to control Salmonella colonization in several European countries. Yet, because of the undefined number and types of micro-organisms present in mixed cultures, the system has not been widely accepted in the United States. One drawback to the widespread use of this method has been the fact that the composition of the product cannot be standardized, and thus the product cannot be stored or produced on a large scale without changes in composition and effectiveness. Also, because the starting material is always the intestinal content of an adult fowl, the product may contain pathogenic viruses, bacteria, or parasites, which may be dangerous to the health of the chicks. Further still, the U.S. Food & Drug Administration has recently required that all undefined cultures must be approved.

SUMMARY OF THE INVENTION

We have now discovered defined probiotics or compositions of bacteria effective for controlling or inhibiting Salmonella colonization of swine. The probiotics are comprised of at least partially characterized populations or cultures of substantially biologically pure bacteria which include:

*Enterococcus faecalis,*

*Streptococcus bovis,*

*Clostridium clostridiforme,*

*Clostridium symbiosum,*

*Clostridium ramosum,*

*Bacteroides fragilis,*

*Bacteroides distasonis,*

*Bacteroides vulgatus,*

*Bacteroides thetaiotamicron,* and

*Bacteroides caccae.*

In use, the probiotics are administered to the subject swine in an amount effective for inhibiting Salmonella colonization thereof. The above-mentioned probiotics may also be combined with a conventional feed, providing a novel feed product which may be orally ingested by the swine.

In accordance with this discovery, it is an object of this invention to provide an improved method and composition for controlling Salmonella colonization in swine.

Other objects and advantages of this invention will become obvious from the ensuing description.

DETAILED DESCRIPTION OF THE INVENTION

The probiotics of this invention are effective for controlling Salmonella colonization of swine when administered thereto, reducing the shedding of Salmonella from the gastrointestinal tract, reducing the average Salmonella concentration in the swine population, and/or lowering the percentage swine colonized by the pathogen. The invention may be practiced with any type of swine, including but not limited to domestic pigs and hogs. Upon administration to swine, the probiotics provide consistent protection against a variety of Salmonella, especially *S. cholerasuis* and *S. typhimurium.*

The probiotics were developed from the ceca of Salmonella-free pigs. As described in more detail in Example 1, the ceca from the pigs were recovered, inoculated into a suitable culture medium, and immediately subjected to continuous-flow culture conditions at a specified media turnover until a steady-state or equilibrium was achieved. When recovered and administered to swine, the resultant steady state culture, which has been designated Pcf1, demonstrated significant effectiveness as a probiotic for the control of Salmonella colonization of the treated animals.

Steady state culture Pcf1 is composed of a stable mixture of no more than 40 species of facultative and anaerobic bacteria. The composition of Pcf1 has been partially characterized, and includes populations of at least the following substantially biologically pure bacteria:

Enterococcus faecalis,
Streptococcus bovis,
Clostridium clostridiforme,
Clostridium symbiosum,
Clostridium ramosum,
Bacteroides fragilis,
Bacteroides distasonis,
Bacteroides vulgatus,
Bacteroides thetaiotamicron, and
Bacteroides caccae.

Steady state culture Pcf1 may be used directly as a probiotic, or stored for later use. With respect to the latter, the culture may be stored as a mixture as indicated, or the individual bacteria may isolated, stored and subsequently recombined.

Additional cultures having efficacy as probiotics for the control of Salmonella in swine may be derived from steady state culture Pcf1. In accordance with one alternative embodiment, the number of species in steady state culture Pcf1 may be reduced by subjecting the culture to serial dilution. Continuous-flow culture may then be resumed using the serially diluted culture as an inoculum until steady state is again achieved. This process may also be repeated using the new steady state cultures as inocula to obtain additional steady state cultures having successively reduced populations.

Using serial dilution in this manner, two additional stable, steady state cultures, designated Pcf2 and Pcf3, have been derived from Pcf1. While these cultures are composed of fewer species of bacteria than Pcf1, they nonetheless retain effectiveness for use as probiotics in swine. Upon analysis, it has been determined that steady state culture Pcf3 is composed of the ten species of bacteria identified above. As with Pcf1, steady state cultures Pcf2 and Pcf3 may also be used directly as a probiotic, or stored for later use, either as a mixture or the individual bacteria may isolated, stored and subsequently recombined.

Steady state cultures Pcf1 and Pcf3 were deposited under the Budapest Treaty in the American Type Culture Collection (10801 University Blvd., Manassas, Va. 20110-2209, USA) on Sep. 17, 1997, and have been assigned Deposit No. ATCC 202036 and ATCC 202037, respectively. The individual strains of Pcf1 and Pcf3 are characterized in Examples 1 and 2.

The compositions of the steady state cultures Pcf1 or Pcf3 may also be modified by removing one or more species of bacteria from their populations, with little or no reduction in efficacy. For example, without being limited thereto, it is envisioned that strains of bacteria that are redundant, that is those genera having multiple strains or species, may be deleted without significantly decreasing efficacy.

In the preferred embodiment, the probiotic is composed of the mixture of bacteria from the deposited steady state cultures Pcf1 or Pcf3. However, in another alternative embodiment, many of the bacteria to be used may be obtained from known or standard strains, or from isolates recovered from swine. For example, without being limited thereto, one or more other strains of Enterococcus, Streptococcus, Clostridium, or Bacteroides, may be substituted for the strains of the same genus or species in the deposited steady state cultures. To enhance efficacy when using stock cultures of known strains, the bacteria may be adapted to the swine by passage therethrough, preferably together with the other organisms from the steady state culture, followed by their subsequent retrieval and isolation from droppings or cecal contents. When swine isolates are used, the bacteria may be individually isolated and recovered from fecal droppings or cecal contents of adult swine using techniques conventional in the art or as described by DeLoach et al. [U.S. Pat. No. 5,308,615], the contents of which are incorporated by reference herein.

It is envisioned that some of the strains of the bacteria of this invention may also be optionally selected for the ability to adhere to the epithelial cells of the alimentary tract of the subject swine in accordance with the technique of Nurmi et al., U.S. Pat. No. 4,689,226, the contents of which are incorporated by reference herein.

Any cultures resulting from a modification of steady state cultures Pcf1 or Pcf3 may be optionally screened to select those compositions which demonstrate optimal efficacy for the inhibition Salmonella colonization of the target animal. In one embodiment, screening may be conducted in vivo with Salmonella challenge as is conventional in the art and described in Examples 3–7. Briefly, the steady state culture is administered to Salmonella-free animals as described herein. After a period of time sufficient for the culture to become established in the gut, usually after about one day, the animals are challenged with a viable culture of Salmonella, incubated, and subsequently killed and the cecal contents analyzed for Salmonella colonization. Effective inhibition of Salmonella colonization is indicated by a reduced incidence of Salmonella shedding, a reduced average Salmonella concentration (CFU), or a lower percentage of animals colonized, in the treated population relative to an untreated control.

Large quantities of the probiotics of this invention may be produced by either batch or continuous culture of the bacteria in a suitable culture medium using anaerobic culture techniques conventional in the art. Of these, continuous culture is of particular advantage, because the steady state cultures are exceedingly stable and may be maintained indefinitely under steady state culture. The inoculum for the large scale culture may be a sample or seed of the steady state culture, the deposit, or stock cultures or substantially biologically pure isolates of the bacteria. The bacteria may be cultured in combination, or in separate culture media and subsequently combined for ease of standardization. In accordance with the latter technique, the final concentration of each bacteria should be between about $10^8$ to $10^9$ organisms/ml prior to combination. However, the practitioner skilled in the art will recognize that the concentration is not critical and may vary. Generally, when large scale production is conducted in batch culture, the culture should be incubated about 6–72 hours before harvesting.

The use of the probiotic of this invention is not affected by the particular method of production; probiotic produced by any of the above-described methods may be used in the same manner. Following production, the cultures of bacteria may be administered directly to the subject animal either singly or in combination. Optionally, the probiotic may be further formulated with a suitable carrier including, but not limited to lactose or skim milk, or combined with a small amount of feed for use as a premix. The cultures may also be freeze dried for storage stability and ease of handling. Such freeze dried cultures may be directly administered to the animal or, in the alternative, reconstituted prior to use. Of special note, one or all of the bacteria may be encapsulated using techniques conventional in the art, including, but not limited to encapsulation in an alginate gel. Without wishing to be bound by theory, it is believed that encapsulation in this manner may prevent some bacteria from reducing the concentration of lactic acid in the upper intestinal tract to undesirable levels. It may also protect the bacteria and allow them to reach the ceca, where lactic acid utilization is desirable.

The probiotic of this invention may also be combined with other substantially biologically pure bacteria which are effective for control of Salmonella in domestic animals or swine and especially those bacteria producing lactic acid or volatile fatty acids. Without being limited thereto, other suitable bacteria include Peptostreptococcus or Propionibacterium species. Other adjuvants conventional or known in the art for the treatment of domestic animals and swine, and particularly for the inhibition or treatment of enteropathogens, may be added to the probiotic. Suitable adjuvants may include, for example, antitoxins, deworming agents, or selected antibiotics as described by Hogg ("Digestive System Diseases", In: 1984 Yearbook of Agriculture: Animal Health Livestock and Pets, U.S. Government Printing Office, 1984-451-784, pp. 290–293). Non-therapeutic levels of some antibiotics may also be administered to the swine as is conventional in the art. However, the use of any antibiotics which may deleteriously effect the efficacy of the probiotics should be avoided. When used, such antibiotics may be administered in combination with or apart from the probiotic.

While the probiotic of this invention is primarily administered or introduced to the alimentary tract by combining with the feed or water of the animal followed by oral ingestion thereof, it is envisioned that it may also be administered orally by spraying or misting the formulation directly into the animalls oral cavity. Still other alternatives include injection directly into the gastrointestinal tract.

Administration of the probiotic may be at any time during the life of the animal. However, in the preferred embodiment the probiotic is administered to newborn swine or piglets within about 4 hours of birth, and repeated approximately 24 hours later.

The probiotic is administered in an amount effective to substantially inhibit the Salmonella colonization in the treated swine, which may include one or more of reducing Salmonella shedding, reducing the average Salmonella concentration, or lowering the percentage of animals colonized, in comparison with untreated animals. Suitable amounts may be readily determined by the practitioner skilled in the art, and will vary somewhat with the age and size of the animal. In the preferred embodiment, when treating newborn swine, 5 ml doses of the active steady state cultures are administered orally.

The following examples are intended only to further illustrate the invention and are not intended to limit the scope of the subject matter which is defined by the claims.

EXAMPLE 1

Preparation of Probiotic

Initial Inoculum. The initial inoculum was obtained from the ceca of a 5 week old commercial pig (reared at the USDA-FAPRL in College Station, Tex.), maintained on a typical grower hog diet in the absence of antibiotics. The pig was sacrificed and its cecal contents immediately taken into a anaerobic chamber (Coy Laboratory Products, Ann Arbor, Mich.) and a 50 gram portion was immediately used as a seed inoculum in a continuous-flow culture apparatus. The remaining cecal contents were mixed with 5% glycerol and stored at −70° Celsius. All procedures were performed anaerobically under sanitary conditions.

Continuous Flow Apparatus. The continuous flow culture was conducted in a BioFlo I fermenter (New Brunswick Scientific Co., Edison, N.J.) fitted with a 2.0 l chemostat vessel (Wier type) with an 1150 ml working volume. When the culture was grown and maintained under continuous flow conditions, the following parameters were used:

dilution rate of $0.0416^{-1}$ (corresponding to a flow rate of 0.80 ml/minute and a vessel turnover time of 24 hr.), temperature of 39° C., and agitation rate of 200 rpm.

Anaerobic conditions were maintained by flushing the vessel with a constant stream of $O_2$-free $CO_2$.

Growth of Cecal Organisms Under Continuous Flow Conditions. The medium used was Viande Levure (VL) broth medium (pH 5.5). Medium was prepared in a 13.3 l PYREX vessel, autoclaved for 1.5 hrs at 15 psi. The medium components were:

| medium component | grams/liter |
| --- | --- |
| tryptose | 10 |
| yeast extract | 5 |
| NaCl | 5 |
| beef extract | 2.4 |
| 1-cysteine HCL | 0.6 |
| Glucose | 2.5 |

After sterilization the medium was put under an atmosphere of $O_2$-free $CO_2$ and allowed to cool to room temperature.

The 1150 ml chemostat vessel was filled with sterile VL medium and allowed to sit 48 hours prior to inoculation with cecal contents to ensure sterility. The chemostat was inoculated with 50 g of the cecal contents and immediately incubated anaerobically in continuous-flow culture as described above. Samples for analysis of volatile fatty acids and pH were taken daily. The culture reached steady state conditions after 6 days with a pH of 6.1. This culture was designated Pcf1. Steady state conditions were assumed when culture pH, $OD_{600}$ and volatile fatty acid concentrations remained approximately constant.

After steady state conditions were achieved, a second culture was developed from Pcf1 by a doing 5 serial 1:10 dilutions of Pcf1 under sterile conditions. The final dilution was then used to inoculate a second chemostat filled with sterile VL medium and the continuous-flow culture was repeated as described above until a steady state was achieved. This second steady state culture was designated Pcf2. A third culture was then developed from Pcf2 by repeating this serial dilution/continuous-flow culture process. Pcf2 was serially diluted at a ratio of 1:10 a total of 8 times. The dilution was used to inoculate another chemostat and continuous-flow culture was again repeated under the same conditions until a steady state was achieved. This third steady state culture was designated Pcf3.

Samples of the continuous-flow cultures were collected aseptically, plated onto solid culture media to isolate pure colonies, and the individual isolates characterized, in substantially the same manner described in Nisbet et al. (U.S.

Pat. No. 5,478,557) the contents of which are incorporated by reference herein. Ten bacterial isolates were identified in the steady state culture Pcf3. The 10 bacterial isolates were identified utilizing biochemical and enzymatic procedures and antimicrobial susceptibility profiles conventional in the art (Holdeman et al., 1977, Anaerobe Laboratory Manual, 4th ed., Virginia Polytechnic Institute and State University, Blacksburg, Va.; Farmer et al., 1985, J. Clin. Microbiol., 21:46–76; Lennette et al., 1985, Clinical Microbiology, 4th ed., American Society for Microbiology, Washington, D.C.; and Devriese et al., 1987, Int. J. Syst. Bacteriol., 37: 257–259, the contents of each of which are incorporated by reference herein). The results for steady state culture Pcf3 are described in Example 2. Because Pcf3 was derived from Pcf1 by serial dilution, Pcf1 must contain the same isolates.

The bacteria in steady state culture Pcf3 were identified as:

Enterococcus faecalis,

Streptococcus bovis,

Clostridium clostridiforme,

Clostridium symbiosum,

Clostridium ramosum,

Bacteroides fragilis,

Bacteroides distasonis,

Bacteroides vulgatus,

Bacteroides thetaiotamicron, and

Bacteroides caccae.

The continuous-flow culture, thus characterized to be composed of 10 bacterial isolates, demonstrated compatible growth in mixed culture, viability in an acid environment (pH 5.0 to 6.5), and the production of volatile fatty acids (VFA) as fermentation end products.

The steady state or competitive exclusion cultures Pcf1 and Pcf3, including all 10 of the above-mentioned bacterial strains, were deposited under the Budapest Treaty in the American Type Culture Collection (10801 University Blvd., Manassas, Va. 20110-2209, USA) on Sep. 17, 1997, and were assigned Deposit No. ATCC 202036 and 202037, respectively.

EXAMPLE 2

Characterization of Bacteria

Each of the 10 bacterial isolates from example 1 was characterized. Analyses were conducted using substantially the same techniques described in Nisbet et al. (U.S. Pat. No. 5,478,557). The results for each of the isolates are described hereinbelow. All bacteria were identified according to standard culture and biochemical criteria.

Isolate Number 1

Cellular characteristics. Bacterium 1 was a gram-positive, nonmotile, coccus.

Culture and colonial characteristics. Bacterium 1 was facultative anaerobic, exhibiting good growth on blood agar when incubated either aerobically or anaerobically. The colonies were nonhemolytic. The bacterium exhibited good growth on bile esculin and m enterococcus agar when incubated aerobically at 37° C. and 45° C. The bacterium hydrolyzed esculin. The bacterium also exhibited good growth in tryptic soy broth at 10° C.

Catalase and oxidase tests. Bacterium 1 was catalase-negative and oxidase-negative.

API RAPID STREP system tests (Analytab Products, Plainview, N.Y.). Results for bacterium 1 are listed in Table 1.

Additional tests. Bacterium 1 exhibited good growth in salt tolerance medium for gram-positive cocci. The bacterium was tellurite tolerant and vancomycin-sensitive.

Bacterial identification. Using the above results, bacterium 1 was identified as Enterococcus faecalis 2.

Isolate Number 2

Cellular characteristics. Bacterium 2 was a gram-positive, nonmotile, coccus.

Culture and colonial characteristics. Bacterium 2 was facultative anaerobic, exhibiting good growth on blood agar when incubated either aerobically or anaerobically. The colonies were nonhemolytic. The bacterium exhibited good growth on bile esculin and m enterococcus agar when incubated aerobically at 37° C. and 45° C. The bacterium hydrolyzed esculin. The bacterium failed to produce visible growth in tryptic soy broth at 10° C. The bacterium failed to produce visible growth in salt tolerance medium for gram-positive cocci. The bacterium was not tellurite tolerant, but was vancomycin sensitive. Catalase and oxidase tests. Bacterium 2 was catalase-negative and oxidase-negative.

API RAPID STREP system tests. Results for bacterium 2 are listed in Table 2.

Bacterial identification. Using the API RAPID STREP identification along with the above results, bacterium 2 was identified as S. bovis biotype 1.

Isolate Number 3

Cellular characteristics. Bacterium 3 was a gram-variable, sporeforming, bacillus. The cells had pointed ends and occurred singly and in pairs. Spores were oval and subterminal.

Culture and colonial characteristics. Bacterium 3 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were large, white, slightly peaked, with slightly scalloped edges, and nonhemolytic.

API AN-IDENT system tests (Analytab Products, Plainview, N.Y.). Results for bacterium 3 are listed in Table 3.

GC results. The amounts of VFAs produced in PYG cultures by bacterium 3 are listed in Table 4.

PRESUMPTO PLATE tests. Results for bacterium II.1 are listed in Table 5.

Differentiation disks results. Bacterium 3 was sensitive to kanamycin, vancomycin, rifampin, and penicillin, but was resistant to colistin, and erythromycin.

Microbial Identification System based on Similarity Index. The MIDI microbial system of identification through the whole cell cellular fatty acid content identified bacterium 3 as Clostridium clostridiiforme with a similarity index of 88%. Using the MIDI identification along with the above results, bacterium 3 was identified as C. clostridiiforme.

Isolate Number 4

Cellular characteristics. Bacterium 4 was a gram-positive, sporeforming, bacillus. The cells had pointed ends and occurred singly and in pairs.

Culture and colonial characteristics. Bacterium 4 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were medium, grayish, flat, with slightly scalloped edges, and nonhemolytic.

Nitrate test. Bacterium 4 was nitrate-positive.

API AN-IDENT system tests. Results for bacterium 4 are listed in Table 6.

GC results. The amounts of VFAs produced in PYG cultures by bacterium 4 are listed in Table 7.

PRESUMPTO PLATE tests. Results for bacterium 4 are listed in Table 8.

Differentiation disks results. Bacterium 4 was sensitive to kanamycin, vancomycin, rifampin, and penicillin, but resistant to colistin and erythromycin.

Microbial Identification System based on Similarity Index. The MIDI microbial system of identification through the whole cell cellular fatty acid content identified bacterium II.2 as *Clostridium symbiosum* CFA group 2 with a similarity index of 81%. Using the MIDI identification along with the above results, bacterium II.2 was identified as *C. symbiosum*.

Isolate Number 5

Cellular characteristics. Bacterium 5 was a gram-variable, sporeforming, bacillus. The cells were long and thin. The spores were round and terminal.

Culture and colonial characteristics. Bacterium 5 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were medium, gray-green, raised to convex, entire with scalloped edges, and nonhemolytic.

Nitrate test. Bacterium 5 was nitrate-negative.

API AN-IDENT system tests. Results for bacterium 5 are listed in Table 9.

Additional tests. Bacterium 5 was sensitive to vancomycin and rifampin-resistant.

Bacterial identification. Using the API AN-IDENT identification along with the above results, bacterium 5 was identified as *Clostridium ramosum*.

Isolate Number 6

Cellular characteristics. Bacterium 6 was a gram-negative, bacillus. The cells were coccobacilli or straight bacilli of variable length.

Culture and colonial characteristics. Bacterium 6 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were slightly umbonate, medium, white, circular with entire edges. The bacterium exhibited good growth on Bacteroides Bile Esculin Agar (BBE) with esculin hydrolysis evident.

API AN-IDENT system tests. Results for bacterium 6 are listed in Table 10.

PRAS (PY) carbohydrate fermentation tests. For bacterium 6, the pH values are listed in Table 11.

Presumpto plate tests. Results for bacterium 6 are listed in Table 12.

Differentiation disks results. Bacterium 6 was sensitive to rifampin, but resistant to penicillin, kanamycin, colistin, and vancomycin.

Bacterial identification. Using the API AN-IDENT identification along with the above results, bacterium 6 was identified as *Bacteroides fragilis*.

Isolate Number 7

Cellular characteristics. Bacterium 7 was a gram-negative, bacillus. The cells were straight bacilli with rounded ends and occurred singly.

Culture and colonial characteristics. Bacterium 7 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were convex, medium, yellow-white, circular with entire edges. The bacterium exhibited good growth on Bacteroides Bile Esculin Agar (BBE) with esculin hydrolysis evident.

API AN-IDENT system tests. Results for bacterium 7 are listed in Table 13.

PRAS (PY) carbohydrate fermentation tests. For bacterium 7, the pH values are listed in Table 14.

Presumpto plate tests. Results for bacterium 7 are listed in Table 15.

Differentiation disks results. Bacterium 7 was sensitive to rifampin, but resistant to penicillin, kanamycin, colistin, and vancomycin.

Bacterial identification. Using the API AN-IDENT identification along with the above results, bacterium 7 was identified as *Bacteroides distasonis*.

Isolate Number 8

Cellular characteristics. Bacterium 8 was a gram-negative. bacillus. The cells were coccobacilli, occurred singly and occasionally in pairs.

Culture and colonial characteristics. Bacterium 8 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were convex, white, small, and circular with entire edges. The bacterium exhibited good growth on Bacteroides Bile Esculin (BBE), but esculin was not hydrolyzed.

API AN-IDENT system tests. Results for bacterium 8 are listed in Table 16.

PRAS (PY) carbohydrate fermentation tests. For bacterium 8, the pH values are listed in Table 17.

Presumpto plate tests. Results for bacterium 8 are listed in Table 18.

Differentiation disks results. Bacterium 8 was sensitive to rifampin, but resistant to penicillin, kanamycin, colistin, and vancomycin.

Bacterial identification. Using the above results, bacterium 8 was identified as *Bacteroides vulgatus*.

Isolate Number 9

Cellular characteristics. Bacterium 9 was a gram-negative, bacillus. The cells stained irregularly, were pleomorphic bacilli with rounded ends, and occurred singly and in pairs.

Culture and colonial characteristics. Bacterium 9 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were convex, medium, white, circular with entire edges. The bacterium exhibited good growth on Bacteroides Bile Esculin Agar (BBE) with esculin hydrolysis evident.

API AN-IDENT system tests. Results for bacterium 9 are listed in Table 19.

PRAS (PY) carbohydrate fermentation tests. For bacterium 9, the pH values are listed in Table 20.

Presumpto plate tests. Results for bacterium 9 are listed in Table 21.

Differentiation disks results. Bacterium 9 was sensitive to rifampin, but resistant to penicillin, kanamycin, colistin, and vancomycin.

Bacterial identification. Using the API An-IDENT identification along with the above results, bacterium 9 was identified as *Bacteroides thetaiotamicron*.

Isolate Number 10

Cellular characteristics. Bacterium 10 was a gram-negative, bacillus. The cells were coccobacilli, and occurred singly.

Culture and colonial characteristics. Bacterium 10 was obligate anaerobic, exhibiting good growth on Anaerobic Brucella Blood Agar (BRU) when incubated under anaerobic conditions, but failed to grow on BRU when incubated aerobically. After 3 days anaerobic incubation on BRU, the colonies were convex, small to medium, whitish, circular with entire edges. The bacterium exhibited good growth on Bacteroides Bile Esculin Agar (BBE) with esculin hydrolysis evident.

API AN-IDENT system tests. Results for bacterium 10 are listed in Table 22.

PRAS (PY) carbohydrate fermentation tests. For bacterium 10, the values are listed in Table 23.

Presumpto plate tests. Results for bacterium 10 are listed in Table 24.

Differentiation disks results. Bacterium 10 was sensitive to rifampin, but resistant to penicillin, kanamycin, colistin, and vancomycin. Bacterial identification. Using the above results, bacterium 10 was identified as *Bacteroides caccae*.

EXAMPLE 3

In Vivo Experiments With Baby Pigs

Experiments were performed to determine the efficacy of Pcf1 and Pcf3 for decreasing salmonellae cecal colonization, and salmonellae shedding in baby pigs.

Experimental Design. Baby piglets were obtained on the day of birth and divided into three groups: Salmonella challenged untreated controls, Salmonella challenged Pcf1 treated piglets, and Salmonella challenged Pcf3 treated piglets. The piglets receiving Pcf1 or Pcf3 were provided by oral gavage 5 ml of active steady state culture per pig, at approximately 4 hours post farrowing and again at weaning. Piglets were challenged via oral gavage with $7 \times 10^6$ cfu Salmonella cholerasuis at one day post weaning.

Shedding of *S. cholerasuis* was determined by culturing rectal swabs collected from each piglet following Salmonella challenge. Cumulative incidence of shedding was determined as number of swabs from each treatment group culturing positive for Salmonella. Salmonella were detected using substantially the same techniques described in Nisbet et al. (U.S. Pat. No. 5,478,557). All piglets were sacrificed two weeks post weaning, and tissues and cecal contents were collected by necropsy and examined for colonization by Salmonella. Tissues examined included tonsils, lungs, bronchial lymph nodes, ileocolic lymph nodes, and ileocolic junction. The results are shown in Table 25.

EXAMPLE 4

The analysis of Example 3 was repeated except that culture Pcf1 was not examined, the Salmonella challenge dosage was $7 \times 10^8$ cfu, and piglets were sacrificed at 7 days post challenge. The results are shown in Table 26.

EXAMPLE 5

The analysis of Example 3 was again repeated except that the Salmonella challenge dosage was $10^8$ cfu and all piglets were sacrificed at 7 days post challenge. The results are shown in Table 27.

EXAMPLE 6

The analysis of Example 3 was again repeated except that culture Pcf3 was not examined, Pcf1 was administered at 4 and 24 hours after birth, the piglets were challenged with $10^4$ cfu *Salmonella cholerasuis* at 48 hours of age, and piglets were sacrificed at 9 days post challenge. The results are shown in Table 28.

EXAMPLE 7

The analysis of Example 3 was repeated yet again except that the Salmonella challenge dosage was $10^4$ cfu, and piglets were sacrificed at 9 days post challenge. The results are shown in Table 29.

It is understood that the foregoing detailed description is given merely by way of illustration and that modifications and variations may be made therein without departing from the spirit and scope of the invention.

TABLE 1

Results of API Rapid STREP system tests with bacterium 1

| Enzyme/Substrate | Reaction | Enzyme/Substrate | Reaction |
|---|---|---|---|
| Pyruvate | +/+ | Ribose | +/+ |
| Hippurate Hydrolysis | +/+ | Arabinose | −/− |
| Esculin Hydrolysis | +/+ | Mannitol | +/+ |
| Pyrrolidonyl-2-napthylamide | +/+ | Sorbitol | +/+ |
| Alpha-galactosidase | +/+ | Lactose | +/+ |
| Beta-glucuronidase | −/− | Trehalose | −/− |
| Beta-galactosidase | −/− | Inulin | −/− |
| Alkaline Phosphatase | −/− | Raffinose | +/+ |
| Leucine Arylamidase | +/+ | Starch | +/+ |
| Arginine Dihydrolase | +/+ | Glycogen | −/− |

*Data of replicate 1/replicate 2.

TABLE 2

Results of API Rapid STREP system tests with bacterium 2

| Enzyme/Substrate | Reaction | Enzyme/Substrate | Reaction |
|---|---|---|---|
| Pyruvate | +/+ | Ribose | −/− |
| Hippurate Hydrolysis | −/− | Arabinose | −/− |
| Esculin Hydrolysis | +/+ | Mannitol | +/+ |
| Pyrrolidonyl-2-napthylamide | −/− | Sorbitol | −/− |
| Alpha-galactosidase | +/+ | Lactose | +/+ |
| Beta-glucuronidase | −/− | Trehalose | +/+ |
| Beta-galactosidase | −/− | Inulin | −/− |
| Alkaline Phosphatase | −/− | Raffinose | +/+ |
| Leucine Arylamidase | +/+ | Starch | +/+ |
| Arginine Dihydrolase | −/− | Glycogen | +/+ |

*Data of replicate 1/replicate 2.

TABLE 3

Results of API An-IDENT system tests with bacterium 3

| Enzyme/Substrate | Reaction | Enzyme/Substrate | Reaction |
|---|---|---|---|
| Indole production | −/− | Leucine aminopeptidase | −/− |
| N-Acetyl-glucosidase | −/− | Proline aminopeptidase | −/− |
| α-Glucosidase | −/− | Pyroglutamic acid arylamidase | −/− |
| α-Arabinosidase | −/− |  |  |
| β-Glucosidase | −/− | Tyrosine aminopeptidase | −/− |
| α-Fucosidase | −/− | Arginine aminopeptidase | −/− |
| Phosphatase | −/− | Alanine aminopeptidase | −/− |
| α-Galactosidase | +/+ | Histidine aminopeptidase | −/− |
| β-Galactosidase | +/+ | Phenylalanine aminopeptidase | −/− |
| Indoxyl-acetate | +/+ |  |  |
| Arginine utilization | +/+ | Glycine aminopeptidase | −/− |
|  |  | Catalase | −/− |

*Data of replicate 1/replicate 2.

TABLE 4

GC results of PYG cultures for bacterium 3

| Volatile Fatty Acids | Controls* PYG | Cultures PYG |
|---|---|---|
| Formic acid | – | – |
| Acetic acid | – | ++ |
| Propionic acid | – | – |
| Isobutyric acid | – | – |
| Butyric acid | – | – |
| Isovaleric acid | – | T |
| Valeric acid | – | – |

The amounts of VFAs are expressed as follows: – = none produced; T = trace amounts produced; + = small amounts produced; ++ = moderate amounts produced; and +++ = large amounts produced.
*Uninoculated PYG broth.

TABLE 5

Results of the Presumpto plate system tests for bacterium 3

| Presumpto Plate No. | Quadrant No. | Agar Media | Growth Ability / Biochemical Tests | Results |
|---|---|---|---|---|
| I | 1 | LD Base | Growth | +++ |
|   |   |   | Indole | – |
|   | 2 | LD-Esculin | Growth | +++ |
|   |   |   | Catalase | – |
|   |   |   | Esculin Hydrolysis | + |
|   | 3 | LD-Egg Yolk | Growth | +++ |
|   |   |   | Lecithinase | – |
|   |   |   | Lipase | – |
|   |   |   | Proteolysis | – |
|   | 4 | LD-Bile | Growth | E |
| II | 1 | LD-DNA | Growth | +++ |
|   |   |   | DNAse | – |
|   | 2 | LD-Glucose | Growth | +++ |
|   |   |   | Glucose Fermentation | + |
|   | 3 | LD-Milk | Growth | +++ |
|   |   |   | Casein Hydrolysis | – |
|   | 4 | LD-Starch | Growth | +++ |
|   |   |   | Starch Hydrolysis | – |
| III | 1 | LD-Mannitol | Growth | +++ |
|   |   |   | Mannitol Fermentation | – |
|   | 2 | LD-Lactose | Growth | +++ |
|   |   |   | Lactose Fermentation | + |
|   | 3 | LD-Rhamnose | Growth | +++ |
|   |   |   | Rhamnose Fermentation | + |
|   | 4 | LD-Gelatin | Growth | +++ |
|   |   |   | Gelatin Hydrolysis | – |

Comparative growth on LD-bile agar compared with LD base: I = less growth; and E = equal growth.

TABLE 6

Results of API An-IDENT system tests for bacterium 4

| Enzyme/Substrate | Reaction | Enzyme/Substrate | Reaction |
|---|---|---|---|
| Indole production | –/– | Leucine aminopeptidase | –/– |
| N-Acetyl-glucosidase | –/– | Proline aminopeptidase | –/– |
| α-Glucosidase | –/– | Pyroglutamic acid arylamidase | –/– |
| α-Arabinosidase | –/– |  |  |
| β-Glucosidase | –/– | Tyrosine aminopeptidase | –/– |
| α-Fucosidase | –/– | Arginine aminopeptidase | –/– |
| Phosphatase | –/– | Alanine aminopeptidase | –/– |
| α-Galactosidase | –/– | Histidine aminopeptidase | –/– |
| β-Galactosidase | –/– | Phenylalanine amino-peptidase | –/– |
| Inoxyl-acetate | –/– |  |  |
| Arginine utilization | +/+ | Glycine aminopeptidase | –/– |
|  |  | Catalase | –/– |

*Data of replicate 1/replicate 2.

TABLE 7

GC results of PYG cultures for bacterium 4

| Volatile Fatty Acids | Controls* PYG | Cultures PYG |
|---|---|---|
| Formic acid | – | – |
| Acetic acid | – | ++ |
| Propionic acid | – | – |
| Isobutyric acid | – | – |
| Butyric acid | – | + |
| Isovaleric acid | – | T |
| Valeric acid | – | – |

The amounts of VFAs are expressed as follows: – = none produced; T = trace amounts produced; + = small amounts produced; ++ = moderate amounts produced; and +++ = large amounts produced.
*Uninoculated PYG broth.

TABLE 8

Results of the Presumpto plate system tests for bacterium 4

| Presumpto Plate No. | Quadrant No. | Agar Media | Growth Ability / Biochemical Tests | Results |
|---|---|---|---|---|
| I | 1 | LD Base | Growth | +++ |
|   |   |   | Indole | – |
|   | 2 | LD-Esculin | Growth | +++ |
|   |   |   | Catalase | – |
|   |   |   | Esculin Hydrolysis | – |
|   | 3 | LD-Egg Yolk | Growth | +++ |
|   |   |   | Lecithinase | – |
|   |   |   | Lipase | – |
|   |   |   | Proteolysis | – |
|   | 4 | LD-Bile | Growth | E |
| II | 1 | LD-DNA | Growth | +++ |
|   |   |   | DNAse | – |
|   | 2 | LD-Glucose | Growth | +++ |
|   |   |   | Glucose Fermentation | + |
|   | 3 | LD-Milk | Growth | +++ |
|   |   |   | Casein Hydrolysis | – |
|   | 4 | LD-Starch | Growth | +++ |
|   |   |   | Starch Hydrolysis | – |
| III | 1 | LD-Mannitol | Growth | +++ |
|   |   |   | Mannitol Fermentation | + |
|   | 2 | LD-Lactose | Growth | +++ |
|   |   |   | Lactose Fermentation | – |
|   | 3 | LD-Rhamnose | Growth | +++ |
|   |   |   | Rhamnose Fermentation | – |
|   | 4 | LD-Gelatin | Growth | +++ |
|   |   |   | Gelatin Hydrolysis | – |

Comparative growth on LD-bile compared with LD base: I = less growth; and E = equal growth.

TABLE 9

Results of API An-IDENT system tests for bacterium 5

| Enzyme/Substrate | Reaction | Enzyme/Substrate | Reaction |
|---|---|---|---|
| Indole production | –/– | Leucine aminopeptidase | –/– |
| N-Acetyl-glucosidase | +/+ | Proline aminopeptidase | –/– |
| α-Glucosidase | +/+ | Pyroglutamic acid arylamidase | –/– |
| α-Arabinosidase | –/– |  |  |
| β-Glucosidase | +/+ | Tyrosine aminopeptidase | –/– |
| α-Fucosidase | –/– | Arginine aminopeptidase | –/– |
| Phosphatase | –/– | Alanine aminopeptidase | –/– |
| α-Galactosidase | –/– | Histidine aminopeptidase | –/– |
| β-Galactosidase | –/– | Phenylalanine amino-peptidase | –/– |
| Indoxyl-acetate | –/– |  |  |
| Arginine utilization | –/– | Glycine aminopeptidase | –/– |
|  |  | Catalase | –/– |

*Data of replicate 1/replicate 2.

TABLE 10

Results of API An-IDENT system tests for bacterium 6

| Enzyme/Substrate | Reaction | Enzyme/Substrate | Reaction |
|---|---|---|---|
| Indole production | −/− | Leucine aminopeptidase | +/+ |
| N-Acetyl-glucosidase | +/+ | Proline aminopeptidase | −/− |
| α-Glucosidase | +/+ | Pyroglutamic acid | +/+ |
| α-Arabinosidase | −/− | arylamidase | |
| β-Glucosidase | +/+ | Tyrosine aminopeptidase | +/+ |
| α-Fucosidase | +/+ | Arginine aminopeptidase | +/+ |
| Phosphatase | +/+ | Alanine aminopeptidase | +/+ |
| α-Galactosidase | +/+ | Histidine aminopeptidase | +/+ |
| β-Galactosidase | −/− | Phenylalanine amino- | +/+ |
| Inoxyl-acetate | +/+ | peptidase | |
| Arginine utilization | −/− | Glycine aminopeptidase | −/− |
| | | Catalase | +/+ |

*Data of replicate 1/replicate 2.

TABLE 11

Results of carbohydrate fermentation tests for bacterium 6

| Carbohydrate Substrate | pH | Results |
|---|---|---|
| Base | 7.0 | − |
| Cellobiose | 6.6 | − |
| Mannitol | 6.8 | − |
| Rhamnose | 6.7 | − |
| Salicin | 6.9 | − |
| Sucrose | 5.4 | + |
| Trehalose | 6.9 | − |
| Xylan | 6.8 | − |
| Xylose | 5.3 | + |

TABLE 12

Results of the Presumpto plate system tests for bacterium 6

| Presumpto Plate No. | Quadrant No. | Agar Media | Growth Ability/ Biochemical Tests | Results |
|---|---|---|---|---|
| I | 1 | LD Base | Growth | +++ |
| | | | Indole | − |
| | 2 | LD-Esculin | Growth | +++ |
| | | | Catalase | + |
| | | | Esculin Hydrolysis | + |
| | 3 | LD-Egg Yolk | Growth | +++ |
| | | | Lecithinase | − |
| | | | Lipase | − |
| | | | Proteolysis | − |
| | 4 | LD-Bile | Growth | E |
| II | 1 | LD-DNA | Growth | +++ |
| | | | DNAse | − |
| | 2 | LD-Glucose | Growth | +++ |
| | | | Glucose Fermentation | + |
| | 3 | LD-Milk | Growth | +++ |
| | | | Casein Hydrolysis | − |
| | 4 | LD-Starch | Growth | +++ |
| | | | Starch Hydrolysis | − |
| III | 1 | LD-Mannitol | Growth | +++ |
| | | | Mannitol Fermentation | − |
| | 2 | LD-Lactose | Growth | +++ |
| | | | Lactose Fermentation | + |
| | 3 | LD-Rhamnose | Growth | +++ |
| | | | Rhamnose Fermentation | − |
| | 4 | LD-Gelatin | Growth | +++ |
| | | | Gelatin Hydrolysis | − |

Comparative growth on LD-bile compared with LD base: I = less growth; and E = equal growth.

TABLE 13

Results of API An-IDENT system tests for bacterium 7

| Enzyme/Substrate | Reaction | Enzyme/Substrate | Reaction |
|---|---|---|---|
| Indole production | −/− | Leucine aminopeptidase | +/+ |
| N-Acetyl-glucosidase | +/+ | Proline aminopeptidase | −/− |
| α-Glucosidase | +/+ | Pyroglutamic acid | −/− |
| α-Arabinosidase | +/+ | arylamidase | |
| β-Glucosidase | +/+ | Tyrosine aminopeptidase | −/− |
| α-Fucosidase | −/− | Arginine aminopeptidase | +/+ |
| Phophatase | +/+ | Alanine aminopeptidase | +/+ |
| α-Galactosidase | +/+ | Histidine aminopeptidase | +/+ |
| β-Galactosidase | −/− | Phenylalanine amino- | +/+ |
| Inoxyl-acetate | +/+ | peptidase | |
| Arginine utilization | −/− | Glycine aminopeptidase | +/+ |
| | | Catalase | +/+ |

*Data of replicate 1/replicate 2.

TABLE 14

Results of carbohydrate fermentation tests for bacterium 8

| Carbohydrate Substrate | pH | Results |
|---|---|---|
| Base | 6.8 | − |
| Cellobiose | 5.4 | + |
| Mannitol | 6.5 | − |
| Rhamnose | 5.6 | + |
| Salicin | 5.2 | + |
| Sucrose | 4.9 | + |
| Trehalose | 5.1 | + |
| Xylan | 6.6 | − |
| Xylose | 5.2 | + |

TABLE 15

Results of the Presumpto plate system tests for bacterium 7

| Presumpto Plate No. | Quadrant No. | Agar Media | Growth Ability/ Biochemical Tests | Results |
|---|---|---|---|---|
| I | 1 | LD Base | Growth | +++ |
| | | | Indole | − |
| | 2 | LD-Esculin | Growth | +++ |
| | | | Catalase | + |
| | 3 | LD-Egg Yolk | Growth | +++ |
| | | | Lecithanase | − |
| | | | Lipase | − |
| | | | Proteolysis | − |
| | 4 | LD-Bile | Growth | E |
| II | 1 | LD-DNA | Growth | +++ |
| | | | DNAse | − |
| | 2 | LD-Glucose | Growth | +++ |
| | | | Glucose Fermentation | + |
| | 3 | LD-Milk | Growth | +++ |
| | | | Casein Hydrolysis | − |
| | 4 | LD-Starch | Growth | +++ |
| | | | Starch Hydrolysis | − |
| III | 1 | LD-Mannitol | Growth | +++ |
| | | | Mannitol Fermentation | − |
| | 2 | LD-Lactose | Growth | +++ |
| | | | Lactose Fermentation | + |
| | 3 | LD-Rhamnose | Growth | +++ |
| | | | Rhamnose Fermentation | + |
| | 4 | LD-Gelatin | Growth | +++ |
| | | | Gelatin Hydrolysis | − |

Comparative growth on LD-bile compared with LD-base: I = less growth; and E = equal growth.

TABLE 16

Results of API An-IDENT system tests for bacterium 8

| Enzyme/Substrate | Reaction | Enzyme/Substrate | Reaction |
|---|---|---|---|
| Indole production | −/− | Leucine aminopeptidase | −/− |
| N-Acetyl-glucosidase | +/+ | Proline aminopeptidase | −/− |
| α-Glucosidase | +/+ | Pyroglutamic acid arylamidase | +/+ |
| α-Arabinosidase | +/+ | | |
| β-Glucosidase | −/− | Tyrosine aminopeptidase | −/− |
| α-Fucosidase | +/+ | Arginine aminopeptidase | +/+ |
| Phosphatase | +/+ | Alanine aminopeptidase | +/+ |
| α-Galactosidase | +/+ | Histidine aminopeptidase | +/+ |
| β-Galactosidase | +/+ | Phenylalanine amino-peptidase | +/+ |
| Inoxyl-acetate | +/+ | | |
| Arginine utilization | −/− | Glycine aminopeptidase | +/+ |
| | | Catalase | −/− |

*Data of replicate 1/replicate 2.

TABLE 17

Results of carbohydrate fermentation tests for bacterium 8

| Carbohydrate Substrate | pH | Results |
|---|---|---|
| Base | 7.1 | − |
| Cellobiose | 6.7 | − |
| Mannitose | 6.9 | − |
| Rhamnose | 6.0 | + |
| Salicin | 6.9 | − |
| Sucrose | 5.1 | + |
| Trehalose | 7.0 | − |
| Xylan | 6.9 | − |
| Xylose | 5.0 | + |

TABLE 18

Results of the Presumpto plate system tests for bacterium 8

| Presumpto Plate No. | Quadrant No. | Agar Media | Growth Ability/ Biochemical Tests | Results |
|---|---|---|---|---|
| I | 1 | LD Base | Growth | +++ |
| | | | Indole | − |
| | 2 | LD-Esculin | Growth | +++ |
| | | | Catalase | − |
| | 3 | LD-Egg Yolk | Growth | +++ |
| | | | Lecithanase | − |
| | | | Lipase | − |
| | | | Proteolysis | − |
| | 4 | LD-Bile | Growth | E |
| II | 1 | LD-DNA | Growth | +++ |
| | | | DNAse | − |
| | 2 | LD-Glucose | Growth | +++ |
| | | | Glucose Fermentation | + |
| | 3 | LD-Milk | Growth | +++ |
| | | | Casein Hydrolysis | − |
| | 4 | LD-Starch | Growth | +++ |
| | | | Starch Hydrolysis | − |
| III | 1 | LD-Mannitol | Growth | +++ |
| | | | Mannitol Fermentation | − |
| | 2 | LD-Lactose | Growth | +++ |
| | | | Lactose Fermentation | + |
| | 3 | LD-Rhamnose | Growth | +++ |
| | | | Rhamnose Fermentation | + |
| | 4 | LD-Gelatin | Growth | +++ |
| | | | Gelatin Hydrolysis | − |

Comparative growth on LD-bile compared to LD base: I = less growth; E = equal growth.

TABLE 19

Results of API An-IDENT system tests for bacterium 9

| Enzyme/Substrate | Reaction | Enzyme/Substrate | Reaction |
|---|---|---|---|
| Indole production | +/+ | Leucine aminopeptidase | −/− |
| N-Acetyl-glucosidase | +/+ | Proline aminopeptidase | −/− |
| α-Glucosidase | +/+ | Pyroglutamic acid arylamidase | −/− |
| α-Arabinosidase | +/+ | | |
| β-Glucosidase | +/+ | Tyrosine aminopeptidase | −/− |
| α-Fucosidase | +/+ | Arginine aminopeptidase | +/+ |
| Phosphatase | +/+ | Alanine aminopeptidase | +/+ |
| α-Galactosidase | +/+ | Histidine aminopeptidase | +/+ |
| β-Galactosidase | −/− | Phenylalanine amino-peptidase | −/− |
| Inoxyl-acetate | +/+ | | |
| Arginine utilization | −/− | Glycine aminopeptidase | −/− |
| | | Catalase | −/− |

*Data of replicate 1/replicate 2.

TABLE 20

Results of carbohydrate fermentation tests for bacterium 9

| Carbohydrate Substrate | pH | Results |
|---|---|---|
| Base | 6.8 | − |
| Cellobiose | 5.5 | + |
| Mannitol | 6.4 | − |
| Rhamnose | 6.3 | − |
| Salicin | 6.2 | − |
| Sucrose | 5.4 | + |
| Trehalose | 5.3 | + |
| Xylan | 5.4 | + |
| Xylose | 5.1 | + |

TABLE 21

Results of the Presumpto ptate system tests for bacterium 9

| Presumpto Plate No. | Quadrant No. | Agar Media | Growth Ability/ Biochemical Tests | Results |
|---|---|---|---|---|
| I | 1 | LD Base | Growth | +++ |
| | | | Indole | + |
| | 2 | LD-Esculin | Growth | +++ |
| | | | Catalase | − |
| | 3 | LD-Egg Yolk | Growth | +++ |
| | | | Lecithinase | − |
| | | | Lipase | − |
| | | | Proteolysis | − |
| | 4 | LD-Bile | Growth | E |
| II | 1 | LD-DNA | Growth | +++ |
| | | | DNAse | + |
| | 2 | LD-Glucose | Growth | +++ |
| | | | Glucose Fermentation | + |
| | 3 | LD-Milk | Growth | +++ |
| | | | Casein Hydrolysis | − |
| | 4 | LD-Starch | Growth | +++ |
| | | | Starch Hydrolysis | − |
| III | 1 | LD-Mannitol | Growth | +++ |
| | | | Mannitol Fermentation | − |
| | 2 | LD-Lactose | Growth | +++ |
| | | | Lactose Fermentation | + |
| | 3 | LD-Rhamnose | Growth | +++ |
| | | | Rhamnose Fermentation | − |
| | 4 | LD-Gelatin | Growth | +++ |
| | | | Gelatin Hydrolysis | − |

Comparative growth on LD-bile compared with LD base: I = less growth; and E = equal growth.

TABLE 22

Results of API An-IDENT system tests for bacterium 10

| Enzyme/Substrate | Reaction | Enzymme/Substrate | Reaction |
|---|---|---|---|
| Indole production | − | Leucine aminopeptidase | + |
| N-Acetyl-glucosidase | + | Proline aminopeptidase | − |
| α-Glucosidase | + | Pyroglutamic acid arylamidase | − |
| β-Arabinosidase | + | | |
| β-Glucosidase | + | Tyrosine aminopeptidase | − |
| β-Fucosidase | + | Arginine aminopeptidase | + |
| Phosphatase | + | Alanine aminopeptidase | + |
| α-Galactosidase | + | Histidine aminopeptidase | + |
| β-Galactosidase | − | Phenylalanine amino-peptidase | + |
| Inoxyl-acetate | + | | |
| Arginine utilization | − | Glycine aminopeptidase | − |
| | | Catalase | + |

TABLE 23

Results of carbohydrate fermentation tests for bacterium 10

| Carbohydrate Substrate | pH | Results |
|---|---|---|
| Base | 6.5 | − |
| Cellobiose | 5.8 | + |
| Mannitol | 6.0 | + |
| Rhamnose | 5.3 | + |
| Salicin | 6.1 | − |
| Sucrose | 5.3 | + |
| Trehalose | 5.2 | + |
| Xylan | 6.2 | − |
| Xylose | 5.1 | + |

TABLE 24

Results of the Presumpto plate system tests for bacterium 10

| Presumpto Plate No. | Quadrant No. | Agar Media | Growth Ability/ Biochemical Tests | Results |
|---|---|---|---|---|
| I | 1 | LD Base | Growth | +++ |
| | | | Indole | − |
| | 2 | LD-Esculin | Growth | +++ |
| | | | Catalase | + |
| | 3 | LD-Egg Yolk | Growth | +++ |
| | | | Lecithinase | − |
| | | | Lipase | − |
| | | | Proteolysis | − |
| | 4 | LD-Bile | Growth | E |
| II | 1 | LD-DNA | Growth | +++ |
| | | | DNAse | + |
| | 2 | LD-Glucose | Growth | +++ |
| | | | Glucose Fermentation | + |
| | 3 | LD-Milk | Growth | +++ |
| | | | Casein Hydrolysis | − |
| | 4 | LD-Starch | Growth | +++ |
| | | | Starch Hydrolysis | − |
| III | | LD-Mannitol | Growth | +++ |
| | | | Mannitol Fermentation | − |
| | 2 | LD-Lactose | Growth | +++ |
| | | | Lactose Fermentation | + |
| | 3 | LD-Rhamnose | Growth | +++ |
| | | | Rhamnose Fermentation | + |
| | 4 | LD-Gelatin | Growth | +++ |
| | | | Gelatin Hydrolysis | − |

Comparative growth on LD-bile compared with LD base: I = less growth; and E = equal growth.

TABLE 25

Incidence of shedding and distribution of *Salmonella choleraesuis* in selected tissues and cecal contents of pigs treated at birth and at weaning with competitive exclusion cultures.

| Treatment group[b] | Cumulative incidence of shedding[c] | Tissue[a] | | | | | Cecal Contents[a] |
|---|---|---|---|---|---|---|---|
| | | Tonsl | Lung | BLym | ILym | IJctn | |
| Untreated | 21/65 (32%) | 2/5 | 1/5 | 0/5 | 5/5 | 2/5 | 3/5 |
| pCF1 | 27/77[d] (35%) | 1/6 | 0/6 | 0/6 | 6/6 | 1/6 | 3/6 |
| pCF3 | 4/52 (8%) | 2/4 | 0/4 | 1/4 | 4/4 | 1/4 | 1/4 |

[a]Number culturing positive for *S. choleraesuis*/number pigs per treatment. Tonsl, tonsils; BLym, bronchial lymph nodes; ILym, ileocolic lymph nodes; IJctn, ileocolic junction. Tissues and cecal contents were collected by necropsy 2 wk post weaning.
[b]Treatments were given via oral gavage (5 ml/pig). Pigs were challenged via oral gavage with $7 \times 10^6$ CFU *S. choleraesuis* one day post weaning and all were necropsied 2 wk post challenge. Reference experiment RA-MSBS/USDA#1-50.
[c]Cumulative incidence is represented as number of rectal swabs culturing positive for *S. choleraesuis*/total number of swabs cultured. All 5 of those pigs untreated and all 6 of those treated with pCF1 shed S. choleraesuis at least once post challenge, only 2 of the 4 pigs treated with pCF3 had shed *S. choleraesuis*.
[d]Rectal swab from one pig was not obtained on day 12 post challenge.

TABLE 26

Incidence of shedding and distribution of *Salmonella choleraesuis* in cecal contents of untreated pigs and pigs treated at birth and at weaning with competitive exclusion culture (pCF3).

| Treatment[a] | Number of pigs shedding | Cumulative incidence of shedding[b] | Distribution of *Salmonella choleraesuis* in cecal contents[c] |
|---|---|---|---|
| None | 7/7 | 40/49 (82%) | 7/7 |
| pCF3 | 9/10 | 32/70 (46%) | 10/10 |

[a]Competitive exclusion culture was given via oral gavage (5 ml/pig). Pigs were challenged via oral gavage with $7 \times 10^8$ CFU *S. choleraesuis* 1 day post weaning and all were necropsied 7 days post challenge. Lymph nodes from all pigs collected at necropsy cultured positive for *S. choleraesuis*. Reference experiment RA-MSBS/USDA#1-70.
[b]Cumulative incidence is represented as number of rectal swabs culturing positive for *S. choleraesuis*/total number of swabs cultured.
[c]CC, cecal contents. *Salmonella choleraesuis* concentrations in cecal contents averaged 4.3 $\log_{10}$ CFU/g for both those pigs administered no treatment and for those administered pCF3, respectively.

TABLE 27

Incidence of shedding and distribution of Salmonella choleraesuis in selected tissues and cecal contents of pigs treated at birth and at weaning with competitive exclusion cultures.

| Treatment[c] | Number of pigs shedding | Cumulative incidence of shedding[d] | Distribution of Salmonella choleraesuis[a] | | | Quantification in cecal contents[b] | |
|---|---|---|---|---|---|---|---|
| | | | ILym | IJctn | CC | Mean | Range |
| none | 10/11 | 42/77 (55%) | 11/11 | 11/11 | 11/11 | 3.0 | 1.0 to 3.6 |
| pCF1 | 8/12 | 20/96 (21%) | 10/12 | 9/12 | 3/12 | 0.9 | 0 to 3.7 |
| pCF3 | 6/8 | 15/56 (27%) | 8/8 | 6/8 | 6/8 | 2.4 | 0 to 4.7 |

[a]ILym, ileocolic lymph nodes; IJctn; ileocolic junction; CC, cecal contents.
[b]$Log_{10}$ CFU/g cecal contents.
[c]Competitive exclusion cultures were given oral gavage (5 ml/pig). Pigs were challenged via oral gavage with $10^8$ CFU S. choleraesius one day post weaning and all were necropised 7 day post challenge. Reference experiment RA-MSBS/USDA#1-139.
[d]Cumulative incidence of shedding is represented as number of rectal swabs culturing positive for S. cholerasuis/total number of swabs cultured.

TABLE 28

Incidence of shedding and distribution of Salmonella choleraesuis in tissues and the gut of baby piglets treated at 4 h and 24 of age with a porcine derived competitive exclusion culture.

| Treatment[c] | Number of animals shedding | Cumulative incidence of shedding[d] | Distribution[a] | | | | Quantification in cecal contents[b] | |
|---|---|---|---|---|---|---|---|---|
| | | | ILym | IJctn | Col | CC | Mean | Range |
| pCF1 | 0/8 | 0/72 (0%) | 3/8 | 4/8 | 2/8 | 3/8 | 1.2 | 0–3.8 |
| Untreated | 3/10 | 4/90 (4%) | 10/10 | 4/10 | 3/10 | 8/10 | 3.6 | 0–6.7 |

[a]ILym, ileocolic lymph nodes; IJctn; ileocolic junction; Col, colon; CC, cecal contents.
[b]$Log_{10}$ CFU/g cecal contents.
[c]Competitive exclusion cultures were given oral gavage (5 ml/pig). Pigs were challenged via oral gavage with $10^4$ CFU S. choleraesius at 48 h of age and all were necropised 9 day post challenge. Reference experiment RA-MSBS/USDA#1-134.
[d]Cumulative incidence of shedding is represented as number of rectal swabs culturing positive for S. cholerasuis/total number of swabs cultured.

TABLE 29

Incidence of shedding and distribution of Salmonella typhimurium in selected tissues and the gut of piglets treated at birth and at weaning with porcine derived competitive exclusion cultures.

| Treatment[c] | Number of animals shedding | Cumulative incidence of shedding[d] | Distribution[a] | | | Quantification in cecal contents[b] | |
|---|---|---|---|---|---|---|---|
| | | | ILym | Col | CC | Mean | Range |
| pCF1 | 9/9 | 36/81 (44%) | 5/9 | 3/9 | 5/9 | 1.3 | 0–1.5 |
| pCF3 | 6/6 | 23/48 (48%) | 5/6 | 6/6 | 6/6 | 2.2 | 1.5–4.3 |
| Untreated | 6/6 | 37/48 (77%) | 3/6 | 2/6 | 6/6 | 1.5 | 1.5 |

[a]ILym, ileocolic lymph nodes; Col, colon; CC, cecal contents.
[b]$Log_{10}$ CFU/g cecal contents.
[c]Competitive exclusion cultures were given oral gavage (5 ml/pig). Pigs were challenged via oral gavage with $10^4$ CFU S. choleraesius one day post weaning and all were necropised 9 day post challenge. Reference experiment RA-MSBS/USDA#2-70.
[d]Cumulative incidence of shedding is represented as number of rectal swabs culturing

We claim:
1. A composition for inhibiting Salmonella colonization of swine comprising populations of substantially biologically pure bacteria, said bacteria comprising at least seven of:
Enterococcus faecalis,
Streptococcus bovis,
Clostridium clostridiforme,
Clostridium symbiosurn,
Clostridium ramosum,
Bacteroides fragilis,
Bacteroides distasonis,
Bacteroides vulgatus,
Bacteroides thetaiotamicron, and
Bacteroides caccae
in an amount effective for inhibiting Salmonella colonization of swine.

2. A composition as described in claim 1 wherein said composition comprises ATCC deposit no. 202036.

3. A composition as described in claim 1 wherein said composition comprises ATCC deposit no. 202037.

4. A composition as described in claim 1 comprising all of said bacteria.

5. A composition as described in claim 1 further comprising a carrier.

6. A composition as described in claim 1, wherein said bacteria are encapsulated.

7. A feed product comprising an animal feed in combination with said composition of claim 1.

8. A method for inhibiting Salmonella colonization of swine comprising administering to said swine a composition including populations of substantially biologically pure bacteria, said bacteria comprising at least seven of:

*Enterococcus faecalis,*

*Streptococcus bovis,*

*Clostridium clostridiforme,*

*Clostridium symbiosum,*

*Clostridium ramosum,*

*Bacteroides fragilis,*

*Bacteroides distasonis,*

*Bacteroides vulgatus,*

*Bacteroides thetaiotamicron,* and

*Bacteroides caccae* wherein said composition is administered in an amount effective for inhibiting Salmonella colonization of the intestine of said swine.

9. A method as described in claim 8 wherein said composition comprises ATCC deposit no. 202036.

10. A method as described in claim 8 wherein said composition comprises ATCC deposit no. 202037.

11. A method as described in claim 8 wherein said composition comprises all of said bacteria.

12. A method as described in claim 8 wherein said swine are selected from the group consisting of domestic pigs and hogs.

13. A method as described in claim 12 wherein said swine are less than about 2 days old.

14. A method as described in claim 8 wherein said populations of bacteria are administered with a carrier.

15. A method as described in claim 8 wherein said bacteria are encapsulated.

16. A method as described in claim 8 wherein the step of administering comprises orally administering said populations to said swine.

17. A method as described in claim 16 wherein the step of administering comprises providing said populations in combination with feed for said swine.

18. A method as described in claim 16 wherein the step of administering comprises providing said populations in combination with water for said swine.

* * * * *